(12) United States Patent
Demming et al.

(10) Patent No.: US 9,738,588 B2
(45) Date of Patent: Aug. 22, 2017

(54) PROCESS FOR CONTINUOUSLY PREPARING DI-$C_{1-3}$-ALKYL SUCCINATES

(71) Applicant: BASF SE, Ludwigshafen (DE)

(72) Inventors: Stefanie Demming, Mannheim (DE); Suman Thotla, Mannheim (DE); Jens Wittenberg, Limburgerhof (DE); Gabriele Iffland, Heidelberg (DE); Christian Brueggemann, Mannheim (DE); Yvonne Hoelzl, Raleigh, NC (US); Wolfgang Siegel, Limburgerhof (DE); Stephan Freyer, Neustadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/888,954

(22) PCT Filed: May 7, 2014

(86) PCT No.: PCT/EP2014/059278
§ 371 (c)(1),
(2) Date: Nov. 4, 2015

(87) PCT Pub. No.: WO2014/180871
PCT Pub. Date: Nov. 13, 2014

(65) Prior Publication Data
US 2016/0083328 A1    Mar. 24, 2016

(30) Foreign Application Priority Data

May 8, 2013 (EP) .................................... 13167052

(51) Int. Cl.
*C07C 67/08* (2006.01)
*B01D 3/14* (2006.01)
*C07C 67/54* (2006.01)

(52) U.S. Cl.
CPC .............. *C07C 67/08* (2013.01); *B01D 3/141* (2013.01); *C07C 67/54* (2013.01)

(58) Field of Classification Search
CPC ............ C07C 67/08; C07C 67/54; B01D 3/14
USPC ....................................................... 560/204
See application file for complete search history.

(56) References Cited

U.S. PATENT DOCUMENTS

| 4,229,589 A * | 10/1980 | Nishimura .............. C07C 67/36 560/190 |
| 5,536,856 A | 7/1996 | Harrison et al. |
| 2006/0252956 A1 | 11/2006 | Miller et al. |
| 2009/0137825 A1* | 5/2009 | Bauduin ............... C07C 29/149 549/263 |

FOREIGN PATENT DOCUMENTS

| CN | 1609093 A | 4/2005 |
| CN | 101525446 A | 9/2009 |
| CN | 101735049 A | 6/2010 |
| CN | 102320963 A | 1/2012 |
| WO | WO-2009/024294 A1 | 2/2009 |

OTHER PUBLICATIONS

Orjuela, A., et al., "Kinetics of Mixed Succinic Acid/Acetic Acid Esterification With Amberlyst 70 Ion Exchange Resin as Catalyst." *Chemical Engineering Journal*, vol. 188, pp. 98-107.
Varadarajan, S., et al., "Catalytic Upgrading of Fermentation-Derived Organic Acids," Biotechnology Progress, 1999, vol. 15, No. 5, pp. 845-854.
International Search Report in International Patent Application No. PCT/EP2014/059278, dated Oct. 27, 2014.

* cited by examiner

*Primary Examiner* — Sudhakar Katakam
*Assistant Examiner* — Kofi Adzamli
(74) *Attorney, Agent, or Firm* — Marshall, Gerstein & Borun LLP

(57) ABSTRACT

The invention relates to a process for continuously preparing di-$C_{1-3}$-alkyl succinates by reacting succinic acid with an $C_{1-3}$-alkanol in the presence of a fixed-bed heterogeneous acidic esterification catalyst in a tubular reactor at a temperature in the range of from 60 to 100° C., wherein a mixture, comprising succinic acid, $C_{1-3}$-alkanol, mono-$C_{1-3}$-alkyl succinate, di-$C_{1-3}$-alkyl succinate and water, is formed in a mixing stage and fed to the entrance of the tubular reactor, and wherein 5 to 75% of the outlet flow rate of the tubular reactor are recycled directly to the mixing stage as a recycle stream, and the molar ratio of $C_{1-3}$-alkanol to succinic acid added to the mixing zone, and not including the $C_{1-3}$-alkanol and succinic acid at the recycle stream, being in the range of from 2.0 to 9.5. The invention furthermore relates to a process for separating the reactor effluent of an esterification of succinic acid with an $C_{1-3}$-alkanol to give di-$C_{1-3}$-alkyl succinates by distillation, wherein the separation is performed in a divided wall column in which $C_{1-3}$-alkanol and water are removed in a top draw of the column, di-$C_{1-3}$-alkyl succinate is removed in a side draw of the column, and wherein mono-$C_{1-3}$-alkyl succinate and succinic acid are removed in a bottom draw of the column.

16 Claims, 1 Drawing Sheet

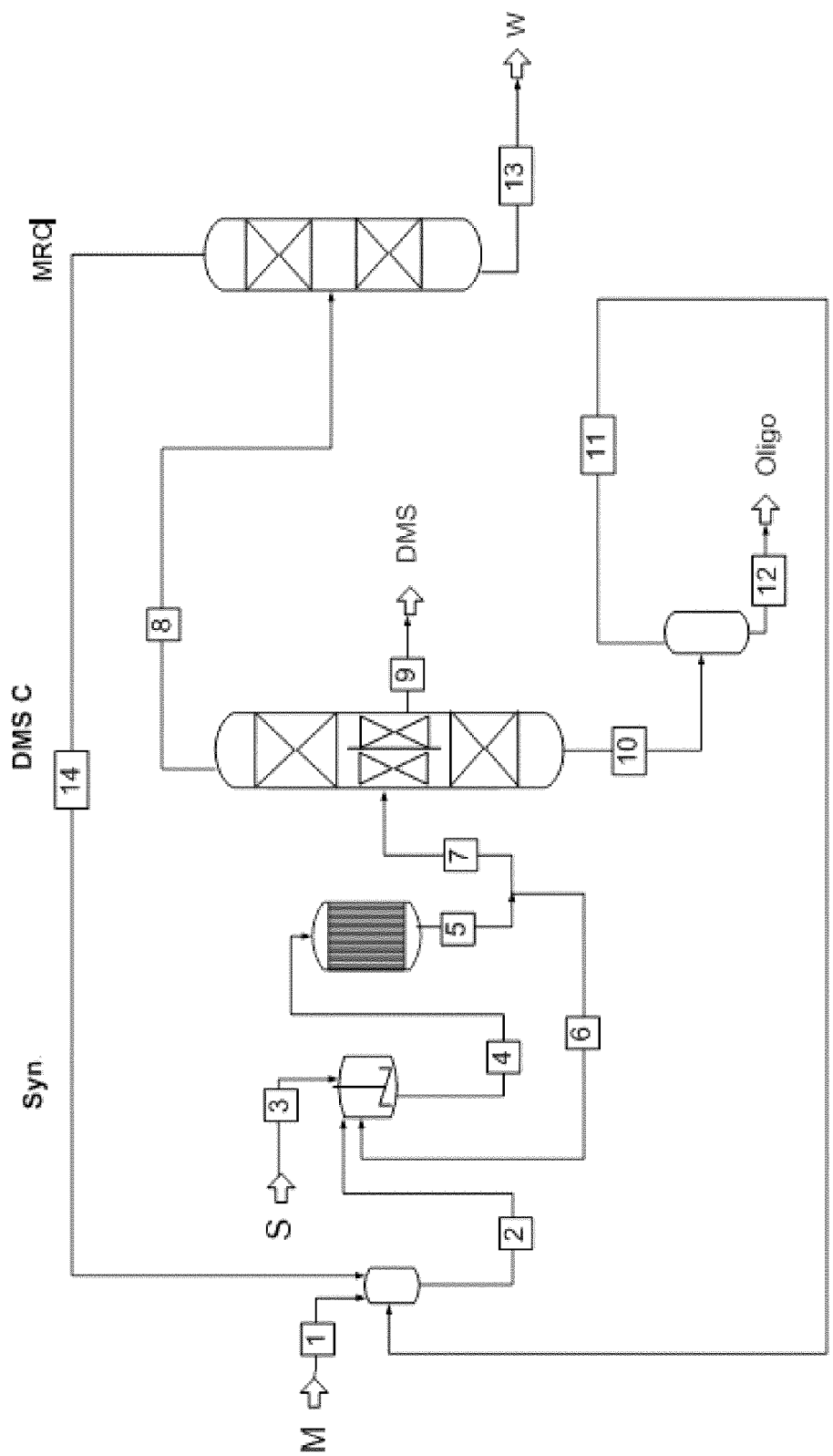

PROCESS FOR CONTINUOUSLY PREPARING DI-$C_{1-3}$-ALKYL SUCCINATES

CROSS-REFERENCE TO RELATED APPLICATION

This is the U.S. national phase of International Application No. PCT/EP2014/059278, filed May 7, 2014, which claims the benefit of European Patent application No. 13167052.3, filed May 8, 2013.

The invention relates to a process for continuously preparing di-$C_{1-3}$-alkyl succinates by reacting succinic acid with a $C_{1-3}$-alkanol in the presence of a heterogeneous acidic esterification catalyst.

The invention furthermore relates to a process for separating the reactor effluent of an esterification of succinic acid with a $C_{1-3}$-alkanol, to give a di-$C_{1-3}$-alkyl succinate by distillation.

Organic carboxylic acids and their esters are important starting materials for chemical synthesis. It is economically important to provide these organic carboxylic acids and their esters in a most cost-efficient manner.

Dicarboxylic acids like succinic acid can be prepared in a fermentation process by employing specific microorganisms. WO 2009/024294 thus relates to the microbial succinic acid production employing a novel bacterial strain designated DD1. In this process glycerol can be employed as a carbon source.

Starting from carboxylic acids like lactic acid or succinic acid, obtained by fermentation, different chemical compounds can be prepared. Different synthesis strategies are disclosed for example in Biotechnol. Prog. 1999, 15, pages 845 to 854.

Different methods for manufacturing alkyl succinate are known from the prior art.

KR-A-2011107967 relates to a method for manufacturing alkyl succinate which involves reacting succinic acid and alcohol in presence of cation exchange resin having sulfonic acid groups as catalyst.

In Chemical Engineering Journal 188 (2012), pages 98 to 107, the liquid phase esterification of succinic acid with ethanol using Amberlyst 70 strong cation exchange resin as catalyst is described. Batch isothermal reactions are performed, and the esterification kinetics are studied.

The alcohol employed in this esterification can be a $C_{1-18}$-alkanol. In the example, octanol is reacted with succinic acid in the presence of Amberlite® IR-120 which is a gel type strongly acidic cation exchange resin. The resulting product is concentrated under reduced pressure and extracted using methanol.

Apart from the synthesis itself, also different work-up sequences for dialkyl succinates are known from the prior art.

CN-A-102320963 relates to the refining and separating of mixed acid dimethyl esters comprising adding mixed acid dimethyl esters into four rectifying towers, separating e.g. 1,4-dimethyl succinate and 1,5-dimethyl glutarate, and discharging high boiling substances. In the sequence of four rectifying towers connected in series, in this sequence typically light components, 1,4-dimethyl succinate, 1,5-dimethyl glutarate, 1,6-dimethyl adipate and high boiling substances are separated.

CN-A-101735049 relates to the production of dibasic acid low-carbon alcohol esters and involves the heating of a mixture of catalyst, dibasic acid and alcohol, esterifying at a preset temperature, supplying the reaction material to a flash evaporator, and condensing.

First, a slurry of catalyst, $C_{4-6}$-dibasic acid and $C_{1-2}$-alcohol is mixed and supplied to a storage tank and afterwards to an esterifying reactor. The reaction material is subsequently supplied to a flash evaporator in which unreacted alcohol and water are discharged from the upper portion of the evaporator. The resulting products are further separated.

CN-A-101525446 relates to the refining of dibasic acid dimethyl ester plasticizing agent by removing light components and heavy components by continuous decompression rectification. First, in a lightness-removing tower, a decompression is carried out, followed by a weight-removing tower to remove the heavy component.

There is still the need for a straight-forward, energy and cost efficient continuous process for an esterification of a succinic acid with low-boiling alcohols to their corresponding esters.

In order to achieve an energy efficient process, the alcohol to acid ratio needs to be balanced to avoid huge recycling quantities. This, however, can lead to significant solubility issues due to the usually limited solubility of succinic acid in the alcohols.

There is furthermore still the need for a straight-forward, energy and cost efficient continuous process for separating the reactor effluent of an esterification of succinic acid with a $C_{1-3}$-alkanol to give di-$C_{1-3}$-alkyl succinate, by distillation. Side reactions should be reduced in this down-stream process.

Thus, the object underlying the present invention is to provide an energy-efficient and therefore cost-efficient process for esterification of succinic acid with low boiling alcohols to their corresponding diesters which avoids the solubility issues mentioned.

Furthermore, for safety and yield issues, the ether formation should be as minimal as possible.

Furthermore, with regard to yield issues, the formation of side products in the downstream processing, i. e. separation, should be avoided. Amongst others, side products could induce fouling in the esterification reactor. But also concerning product purity, the formation of side products should be avoided.

With regard to the process for separating the reactor effluent of an esterification of succinic acid with a $C_{1-3}$-alkanol to give di-$C_{1-3}$-alkyl succinates, by distillation, the object is to provide a separation process, which reduces side reactions, preferably minimizing the back reaction of the diester and the oligomerization reaction. The process should reduce the energy requirement and capital investment.

The object is achieved according to the present invention by a process for continuously preparing di-$C_{1-3}$-alkyl succinates by reacting succinic acid with a $C_{1-3}$-alkanol in the presence of a fixed-bed heterogeneous acidic esterification catalyst in a tubular reactor at a temperature in the range of from 60 to 100° C., wherein a mixture, comprising succinic acid, $C_{1-3}$-alkanol, mono-$C_{1-3}$-alkyl succinate, di-$C_{1-3}$-alkyl succinate and water, is formed in a mixing stage and fed to the entrance of the tubular reactor, wherein 5 to 75%, preferably 5 to 69%, of the outlet flow rate of the tubular reactor are recycled to the mixing stage as a recycle stream, and the molar ratio of $C_{1-3}$-alkanol to succinic acid in the mixture added to the mixing zone and not including the $C_{1-3}$-alkanol and succinic acid of the recycle stream being in the range of from 2.0 to 9.5.

A higher molar ratio in this range may typically be combined with a lower recycle flow rate in this range and vice versa.

The outlet flow rate refers to the reactor effluent.

The object is furthermore achieved by a process for separating the reactor effluent of an esterification of succinic acid with a $C_{1-3}$-alkanol to give di-$C_{1-3}$-alkyl succinates by distillation, wherein the separation is performed in a divided wall column in which $C_{1-3}$-alkanol and water are removed in a top draw of the column, di-$C_{1-3}$-alkyl succinate is removed in a side draw of the column, and wherein mono-$C_{1-3}$-alkyl succinate and succinic acid are removed in a bottom draw of the column.

In the divided wall column a reaction of mono methyl succinate to dimethyl succinate and succinic acid is taking place.

Preferably, the process for continuously preparing di-$C_{1-3}$-alkyl succinates according to the present invention is combined with the process for separating the reactor effluent according to the present invention. This preferred overall process leads to significantly combined advantages, e.g. with regard to energy requirement and capital investment and suppression of side reactions.

According to the present invention it has been found that by recycling 5 to 75%, preferably 5 to 69% of the outlet flow rate of the tubular reactor to the mixing stage, the amount of $C_{1-3}$-alkanol employed can be reduced to a significant extent and at the same time the solubility of succinic acid is not adversely affected. Due to the reduced amount of alkanol employed, the work-up sequence can be significantly reduced in size since only smaller amounts of alkanol have to be removed by distillation and recycled. Consequently, the energy consumption is also lower, since the $C_{1-3}$-alkanol is typically removed by distillation over head.

According to the present invention it has been found that part of the alkanol which does not only function as reagent but also as solvent for the succinic acid, can be replaced by the esterification reactor effluent, and no solubility issues arise and the esterification can be still performed in the liquid phase, thereby obtaining a liquid reactor effluent stream.

If the alkanol to succinic acid ratio is reduced in processes according to the prior art, significant solubility issues arise due to the usually limited solubility of succinic acid in the alkanol. However, in order to achieve an energy efficient process, the alcohol-acid ratio needs to be well balanced to avoid huge recycling quantities.

The process according to the present invention has the further advantage that the ether formation can be minimized. Other side products like oligomers can be removed easily in the downstream processing in a flash distillation.

A distillation sequence according to the present invention furthermore avoids a further formation of side products which would leave the column together with the product.

In the mixing stage, the chemical compounds to be introduced into the tubular reactor are mixed, so that preferably a homogeneous liquid mixture results in which no solids are dispersed. The mixing can be performed in all suitable known types of mixers which can be operated in a continuous or discontinuous manner. Preferably, a continuously operated mixing vessel is employed.

Preferably, the mixture formed in the mixing stage is composed to at least 90 wt-%, preferably at least 95 wt-%, of succinic acid, $C_{1-3}$-alkanol, mono-$C_{1-3}$-alkyl succinate, di-$C_{1-3}$-alkyl succinate and water, based on the mixture formed in the mixing stage.

Preferably, the mixture formed in the mixing stage comprises water in an amount of 10 wt-% or less, more preferably 6 wt-% or less, in particular 5 wt-% or less.

In the process according to the present invention a tubular reactor is employed. The term "a tubular reactor" also encompasses a series of two or more tubular reactors. A tubular reactor has an elongated third dimension, compared to the cross section formed by the first and second dimension, and the reaction mixture flows through the tubular reactor in the direction of this third elongated dimension. Consequently, the tubular reactor has an inlet side and an outlet side and an elongated flow path between the inlet and outlet sides of the reactor. The design of suitable tubular reactors is known. Preferably a plug flow reactor is employed which enables a homogeneous contact of the reaction mixture with the fixed-bed heterogeneous acidic esterification catalyst.

In the esterification, a fixed-bed heterogeneous acidic esterification catalyst is employed which avoids neutralization issues and separation issues arising in the separation of the catalyst from the reaction mixture.

The fixed-bed heterogeneous acidic esterification catalyst is located in the tubular reactor. All heterogeneous acidic esterification catalysts can be employed which accelerate the esterification of succinic acid with $C_{1-3}$-alkanols. Examples of these heterogeneous acidic esterification catalysts are acidic ion exchange resins, which can e.g. be microporous (pore diameter of less than 2 nm, which can be measured by BET- and porosimetry methods) or gel-like. Preferably, the catalyst is selected from Amberlyst® 46, Amberlyst® 15, Amberlyst® 36, Amberlyst® 39, Amberlyst® 131 and Lewatit®K 2621, obtainable from Rohm and Haas. Preferably, the heterogeneous acidic esterification catalyst is an acidic ion exchange resin. Suitable acidic ion exchange resins are described in the prior art references discussed in the introduction above. Preferably, Amberlyst® strong cation exchange resins are employed as catalyst. One example is Amberlyst 70. Also other types of Amberlyst cation exchange resins can be employed according to the present invention.

The catalyst load with the succinic acid is preferably in the range of from 200 to 700 g/l h, more preferably in the range of from 300 to 550 g/l h.

The process according to the present invention is preferably performed in a manner, so that in the effluent of the tubular reaction, the succinic acid, $C_{1-3}$-alkanol, mono-$C_{1-3}$-alkyl succinate, di$C_{1-3}$-alkyl succinate and water are present in equilibrium concentrations. Preferably, in the tubular reactor, the succinic acid conversion is at least 95 wt-%, more preferably at least 98 wt-%, in particular at least 99 wt-%.

According to the present invention, for the esterification a mixture comprising succinic acid, $C_{1-3}$alkanol, mono-$C_{1-3}$-alkyl succinate, di-$C_{1-3}$-alkyl succinate and water is employed. Preferably, the mixture predominantly comprises these substances, i. e. other chemical compounds are present in an amount of 10 wt-% or less, preferably 5 wt-% or less, based on the mixture.

In a more preferred embodiment, the mixture consists of the listed chemical compounds.

The $C_{1-3}$-alkanol can be methanol, ethanol, n-propanol or iso-propanol. Preferably, methanol is employed. Preferably, only one type of alkanol is employed, which is most preferably methanol.

Mono- and diesters of alkanol with succinic acid can be present in the mixture. The diester is denoted di-$C_{1-3}$-alkyl succinate, the monoester mono-$C_{1-3}$-alkyl succinate.

The molar ratio of $C_{1-3}$-alkanol to succinic acid added to the mixing zone, and not including the $C_{1-3}$-alkanol and succinic acid of the recycle stream (from the reactor), is in the range of from 2.0 to 9.5, preferably in the range of from 2.5 to 9.5, more preferably in the range of from 3 to 7, most preferably in the range of from 3 to 4. For example, a molar ratio of 3.5 can be employed.

The amounts of mono- and diester depend on the degree of recycling of the effluent or outlet flow rate of the tubular reactor. According to the present invention 5 to 75%, preferred 5 to 69%, more preferably 25 to 63%, for example 58% of the outlet flow rate of the tubular reactor are recycled to the mixing stage. Typically, the effluent of the tubular reactor can have the following composition, wherein the sum of the constituents is 100 wt-%:

succinic acid 0.5 to 5 wt-%, preferably 0.7 to 2 wt-%
mono-$C_{1-3}$-alkyl succinate: 5 to 30 wt-%, preferably 10 to 20 wt-%, more preferably 13 to 18 wt-%
di-$C_{1-3}$-alkyl succinate: 30 to 70 wt-%, preferably 40 to 55 wt-%, more preferably 45 to 50 wt-%
$C_{1-3}$-alkanol: 10 to 35 wt-%, more preferably 15 to 30 wt-%, more preferably 17 to 27 wt-%
water: 2 to 20 wt-%, preferably 5 to 15 wt-%, more preferably 10 to 15 wt-%
oligomers and side products: 1 wt-% or less, preferably 0.5 wt-% or less, more preferably as low as possible.

The esterification in the tubular reactor is performed at a temperature in the range of from 60 to 100° C., preferably 70 to 90° C., in particular 75 to 85° C., for example 80° C.

The pressure in the tubular reactor is preferably in the range of from 1 to 5 bar, more preferably in the range of from 1 to 3 bar, in particular in the range of from 1 to 2 bar.

Preferably, no gaseous reaction products are removed from the tubular reactor. Preferably, a liquid effluent of the tubular reactor is obtained which is partially recycled and partially transferred to a work-up sequence.

Preferably, from the effluent of the tubular reactor which is not recycled to the mixing stage, di$C_{1-3}$-alkyl succinate is separated by distillation.

The separation can be performed in all types of distillation apparatuses, like flash evaporation or distillation columns. Preferably the separation is performed in a divided wall column in which $C_{1-3}$-alkanol and water are removed in a top draw of the column, di-$C_{1-3}$-alkyl succinate is removed in a side draw of the column, and mono-$C_{1-3}$-alkyl succinate and succinic acid are removed in a bottom draw of the column and preferably recycled to the mixing stage.

A dividing wall column is a distillation column, which contains a dividing wall in the middle part of the distillation column. Thereby, the up-going vapour is split in two streams which flow through the two compartments of the dividing wall column formed by the dividing wall. On the other hand, the down-coming liquid is also split in two streams flowing in the two compartments. The product mixture to be separated enters the divided wall column in the section of the divided wall in one of the chambers separated by the dividing wall. A side draw is taken off the opposite chamber in the height of the dividing wall. At the top of the column, light ends are removed, whereas at the bottom of the column, high boilers are removed. The distillation wall column is a thermodynamically equivalent to a Petlyuk column. The product purity of the middle product is greater than can be achieved in a simple side draw column. Preferably, this side draw product should be in excess of the light and heavy ends, and the light and heavy ends should be present in approximately equal quantities for optimum distillation results. Dividing wall columns for this type of separation can lead to significant reductions in capital costs and energy costs of around 30% each.

The divided wall column preferably contains no heterogeneous acidic esterification catalyst. Preferably, the divided wall column does not contain any additional catalytically active compounds besides the composition of the reactor effluent of the succinic acid esterification with $C_{1-3}$-alkanol.

Preferably, the top draw of the divided wall column is introduced in a second distillation column in which $C_{1-3}$-alkanol is removed in a top draw of the column and preferably recycled to the mixing stage, and water is removed in a bottom draw.

From the bottom draw of the divided wall column, oligomers can be removed in a bottom draw of a flash distillation.

The total reaction and work-up scheme is illustrated in the FIGURE, which is a schematic representation of the process.

In the FIGURE, the left part is the synthesis part of the reaction scheme, the middle part is the dimethyl succinate column (when methanol is employed), and the right hand column is the methanol recovery column.

In the figure, the abbreviations have the following meanings:
SYN: synthesis (esterification)
DMSC: dimethylsuccinate column
MRC: methanol recovery column
M: methanol
S: succinic acid
DMS: dimethyl succinate
Oligo: oligomers
W: water The depicted process set-up basically comprises a mixing vessel, a plug flow reactor including the heterogeneous catalyst and an internal recycle loop, a divided wall column for final product separation via the side draw and a second column for water/alcohol separation, as well as a flash evaporator for removing oligomers.

In the work-up sequence, no heterogeneous catalyst is employed. Thus, the different columns including the divided wall column are free from heterogeneous catalyst.

To prevent blockage during the heterogeneously catalysed reaction of succinic acid with the $C_{1-3}$-alkanol to a succinic acid ester and water in a plug flow reactor, a solution of the succinic acid in the alkanol is usually needed at the entry of the reactor. For the same reason it is preferred to achieve a homogeneous solution at the outlet of the reactor. For the ingoing solution, the minimal equivalent amount of alcohol is therefore determined by the solubility of the acid in the alcohol. The solubility of succinic acid in methanol is in the range of 20-30 wt % for a temperature range of 40-60° C. Based on the observation that some heterogeneous reaction mixtures with a lower alcohol/acid ratio than necessary to achieve a clear solution turned into clear solutions during the course of the reaction, a reaction set-up was created in which one part of the reaction mixture which ideally has reached the reaction equilibrium, is recycled back from the reactor outlet via an internal loop to the reactor entry where it is charged again with alcohol and acid in the desired ratio until the composition of the solubility point is reached. Having passed the reactor, the reaction mass added at the entry of the reactor is separated from the loop and further processed. This set-up allows the optimization of the production costs in respect of methanol recycling cost and acid/intermediate recycling costs.

Since the equilibrium reaction mixture is partially recycled back to the reactor inlet, the water content in the feed is higher resulting in negligible ether formation.

The side reactions in the downstream process are reduced by use of a divided wall column. In this set-up, both, the alcohol and the water leave the column as overhead product. In doing so, the monoester/organic acid catalysed back reaction is minimized. The divided wall column reduces the energy requirement and capital investment. The other advantage of a divided wall column is that light boiling components formed in the side reaction (e. g. anhydride formation leading to methanol and/or water formation) can be separated from the e.g. dimethyl succinate product stream leading to a higher purity product. Monomethyl succinate is converted to dimethyl succinate and succinic acid in the stripping section of the divided wall column which reduces the bottom temperature and supresses the oligomerisation reaction.

The final product, the diester, is separated via the side draw of the divided wall column with negligible amounts of alcohol and water. By employing the divided wall column a significant product contamination with alcohol and water can be excluded since the side reactions can be suppressed.

The composition of the bottom draw of the divided wall column includes predominantly monoester and in addition diester and organic acid, which are recirculated to the feed of the plug flow reactor or the mixing vessel. Due to thermal stress, by-products could be generally formed in the bottom of the column. However, since in the bottom part of the column, a reaction from monoester to either the acid or the diester is taking place, the temperature is reduced in the divided wall column, thus minimizing the formation of side products. The bottom temperature in the divided vided wall column is preferably in the range of from 150 to 165° C. If necessary or required, a flash distillation can be included to dispose possible distillation residues.

The invention is further illustrated by the enclosed examples.

EXAMPLES

I. Experimental

SA: Succinic Acid
MMS: Monomethyl Succinate
DMS: Dimethyl Succinate
MeOH: Methanol 1. Determination of Kinetic Data For the determination of kinetic data a reactor set up was established in which defined solutions of succinic acid in MeOH or succinic acid, dimethyl succinate, monomethyl succinate and water in MeOH were run at 65, 80 or 100° C. through either a 60 ml or a 6 ml plug flow reactor containing a heterogeneous catalyst. Samples of the reaction mixtures were taken before entering and after leaving the reactor. All reaction mixtures used for these trials based on a succinic acid/MeOH ratio of either 1/10, 1/6 or 1/2. Residence times were calculated from the free available reactor space and the measured flow rates.

Example 1

A vessel was charged with 400 g of succinic acid and 1085 g of methanol. The mixture was heated to 60° C. and the solution was transferred via HPLC pump into a heating loop where it was heated to 80° C. and from there into a 60 ml plug flow reactor, equipped with Amberlyst®36 catalyst. The mass flow was determined as 122 g/h. Samples, taken at the outlet of the reactor, determined a molar DMS:MMS:SA ratio of 87.5:12.0:0.5. The composition of the outlet flow was determined as 29.2 wt-% DMS, 3.6 wt-% MMS, 0.1 wt-% SA. 59.5 wt-% MeOH and 7.7 wt-% of water.

Example 2

1505 g of a mixture of 24.7 wt-% of succinic acid, 11.0 wt-% of DMS, 2.9 wt-% of MMS, 57.1% of MeOH and 4.3% of water was charged to a vessel and heated to 60° C. The solution was transferred via HPLC pump into a heating loop where it was heated to 65° C. and from there into a 60 ml plug flow reactor, equipped with Amberlyst®39. The mass flow was determined as 450 g/h. Samples taken at the outlet of the reactor determined a molar DMS:MMS:SA ratio of 57.6% of DMS, 30.3% of MMS and 12.1% of SA. The composition of the outlet flow was determined as 25.8 wt-% of DMS, 12.3 wt-% of MMS, 4.4 wt-% of SA, 9.2 wt-% of water and 48.2% of MeOH.

2. Decomposition of Monomethyl Succinate

Example 3

10 g of MMS (content: 93.6 wt-%) were charged to a vessel with a distillation head. The compound was heated at 180° C. for 21 h. A sample was taken from the liquid which shows a composition of 49.5 wt-% of MMS, 23.4 wt-% of MMS and 15.6 wt-% of SA.

3. Solubility

Example 4

A mixture of 12.9 g of MMS, 0.68 g of DMS, 27.7 g of MeOH and 0.03 g of water was placed in a reactor, heated to 80° C. and charged with 29.8 g of SA. To the suspension were added slowly 80 ml of a solution of 2.50 g of SA, 37.1 g of MMS, 103 g of DMS, 33.8 g of MeOH and 25.1 g of water to give at 80° C. a solution containing 19 wt-% of succinic acid, 19 wt-% of MMS and 29 wt-% of DMS.

These experimental data together with property data, which were derived from literature and/or experimentally determined, were included to simulate the operation of the esterification and the work-up sequence which is depicted in the FIGURE.

II. Calculation

The calculation/simulation was based on the kinetic data of the heterogeneous catalyst Amberlyst® 39. The reaction temperature and pressure were set at 80° C. and 1 bar, respectively. A molar ratio of methanol to succinic acid, added to the mixing zone and not including the $C_{1-3}$-alkanol and succinic acid of the recycle stream, of 3.5 was used. The recycle stream (6) was approximately 58% of the reactor effluent stream (5) or flow rate. The part of the reactor effluent which was not recycled to the mixing stage was fed to a divided wall column for further separation. A top-draw (stream 8), a side-draw (stream 9) and a bottom-draw (stream 10) were removed from this divided wall column. The resulting temperature, pressure, mass flow rate and composition of all streams are listed in the following table:

| Stream: | | 1 | 2 | 3 | 4 | 5 | 6 | 7 |
|---|---|---|---|---|---|---|---|---|
| Temperature | °C. | 45.0 | 90.6 | 45.0 | 80.0 | 90.0 | 90.0 | 90.0 |
| Pressure | bar | 1.0 | 1.0 | 1.0 | 1.0 | 1.0 | 1.0 | 1.0 |
| Mass flow rate | kg/h | 5.51 | 17.82 | 10.12 | 66.52 | 66.52 | 38.58 | 27.94 |
| SA | Wt-% | 0.00 | 5.76 | 99.96 | 17.41 | 1.14 | 1.14 | 1.14 |
| MMS | Wt-% | 0.00 | 17.13 | 0.00 | 14.22 | 16.60 | 16.60 | 16.60 |
| DMS | Wt-% | 0.00 | 13.58 | 0.00 | 32.82 | 50.32 | 50.32 | 50.32 |
| MeOH | Wt-% | 99.90 | 63.47 | 0.00 | 29.09 | 20.84 | 20.84 | 20.84 |
| H2O | Wt-% | 0.10 | 0.06 | 0.04 | 6.46 | 11.10 | 11.10 | 11.10 |

| Stream: | | 8 | 9 | 10 | 11 | 12 | 13 | 14 |
|---|---|---|---|---|---|---|---|---|
| Temperature | °C. | 36.0 | 141.0 | 169.4 | 169.4 | 169.4 | 115.8 | 68.3 |
| Pressure | bar | 0.2 | 0.2 | 0.2 | 0.2 | 0.2 | 1.7 | 1.7 |
| Mass flow rate | kg/h | 8.94 | 12.50 | 6.50 | 6.50 | 0.00 | 3.11 | 5.81 |
| SA | Wt-% | 0.00 | 0.00 | 15.80 | 15.80 | 15.80 | 0.00 | 0.00 |
| MMS | Wt-% | 0.00 | 0.00 | 46.96 | 46.96 | 46.96 | 0.00 | 0.00 |
| DMS | Wt-% | 0.20 | 99.98 | 37.24 | 37.24 | 37.24 | 0.57 | 0.00 |
| MeOH | Wt-% | 65.13 | 0.00 | 0.00 | 0.00 | 0.00 | 0.01 | 99.90 |
| H2O | Wt-% | 34.67 | 0.02 | 0.00 | 0.00 | 0.00 | 99.42 | 0.10 |

The invention claimed is:

1. A process for continuously preparing di-$C_{1-3}$-alkyl succinates by reacting succinic acid with an $C_{1-3}$-alkanol in the presence of a fixed-bed heterogeneous acidic esterification catalyst in a tubular reactor at a temperature in a range of from 60 to 100° C., wherein a mixture, comprising succinic acid, $C_{1-3}$-alkanol, mono-$C_{1-3}$-alkyl succinate, di-$C_{1-3}$-alkyl succinate, and water, is formed in a mixing stage and fed to an entrance of the tubular reactor, and wherein 5 to 75% of an outlet flow rate of the tubular reactor is recycled directly to the mixing stage as a recycle stream, and a molar ratio of $C_{1-3}$-alkanol to succinic acid added to the mixing zone, and not including the $C_{1-3}$-alkanol and succinic acid of the recycle stream, is in the range of from 2.0 to 9.5.

2. The process of claim 1, wherein in the effluent of the tubular reactor the succinic acid, $C_{1-3}$-alkanol, mono-$C_{1-3}$-alkyl succinate, di-$C_{1-3}$-alkyl succinate and water are present in equilibrium concentrations.

3. The process of claim 1, wherein in the tubular reactor the succinic acid conversion is at least 95 wt-%.

4. The process of claim 1, wherein the molar ratio of $C_{1-3}$-alkanol to succinic acid added to the mixing zone, and not including the $C_{1-3}$-alkanol and succinic acid of the recycle stream, is from 3 to 7.

5. The process of claim 1, wherein 25 to 63 wt-% of the effluent of the tubular reactor is recycled to the mixing stage.

6. The process of claim 1, wherein the $C_{1-3}$-alkanol is methanol and dimethyl succinate is prepared.

7. The process of claim 1, wherein the mixture formed in the mixing stage comprises at least 90 wt % of succinic acid, $C_{1-3}$-alkanol, mono-$C_{1-3}$-alkyl succinate, di-$C_{1-3}$-alkyl succinate, and water.

8. The process of claim 1, wherein the mixture formed in the mixing stage comprises water in an amount of 10 wt-% or less.

9. The process of claim 1, wherein the tubular reactor is a plug flow reactor.

10. The process of claim 1, wherein the heterogeneous acidic esterification catalyst is an acidic ion exchange resin.

11. The process of claim 1, wherein from the effluent of the tubular reactor which is not recycled to the mixing stage, di-$C_{1-3}$-alkyl succinate is separated by distillation.

12. The process of claim 11, wherein the separation is performed in a divided wall column in which $C_{1-3}$-alkanol and water are removed in a top draw of the column, di-$C_{1-3}$-alkyl succinate is removed in a side draw of the column, and mono-$C_{1-3}$-alkyl succinate and succinic acid are removed in a bottom draw of the column.

13. The process of claim 4, wherein the molar ratio of $C_{1-3}$-alkanol to succinic acid added to the mixing zone, and not including the $C_{1-3}$-alkanol and succinic acid of the recycle stream, is from 3 to 4.

14. The process of claim 7, wherein the mixture formed in the mixing stage comprises at least 95 wt-% of succinic acid, $C_{1-3}$-alkanol, mono-$C_{1-3}$-alkyl succinate, di-$C_{1-3}$-alkyl succinate, and water.

15. The process of claim 14, wherein the mixture formed in the mixing stage comprises at least 98 wt-% of succinic acid, $C_{1-3}$-alkanol, mono-$C_{1-3}$-alkyl succinate, di-$C_{1-3}$-alkyl succinate, and water.

16. The process of claim 12, wherein the mono-$C_{1-3}$-alkyl succinate and succinic acid removed in the bottom draw of the column are recycled to the mixing stage.

* * * * *